(12) United States Patent
Haddad

(10) Patent No.: US 6,475,150 B2
(45) Date of Patent: Nov. 5, 2002

(54) SYSTEM AND METHOD FOR ULTRASONIC TOMOGRAPHY

(75) Inventor: Waleed Sami Haddad, Dublin, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/728,304

(22) Filed: Dec. 1, 2000

(65) Prior Publication Data

US 2002/0099290 A1 Jul. 25, 2002

(51) Int. Cl.[7] ............................. A61B 8/15; G01N 29/00
(52) U.S. Cl. ............................................ 600/448; 73/602
(58) Field of Search ................................. 600/437, 438, 600/442, 443, 447, 448, 459; 128/915–916; 73/597, 599, 602

(56) References Cited

U.S. PATENT DOCUMENTS

| | | | | | |
|---|---|---|---|---|---|
| 4,222,274 | A | * | 9/1980 | Johnson | 73/607 |
| 4,279,157 | A | * | 7/1981 | Schomberg et al. | 73/618 |
| 4,625,555 | A | * | 12/1986 | Fujii | 73/597 |
| 5,079,951 | A | * | 1/1992 | Raymond et al. | 73/602 |
| 5,305,752 | A | * | 4/1994 | Spivey et al. | 73/602 |
| 5,355,888 | A | * | 10/1994 | Kendall | 600/443 |
| 6,200,266 | B1 | * | 3/2001 | Shokrollahi et al. | 600/438 |

* cited by examiner

Primary Examiner—Francis J. Jaworski
(74) Attorney, Agent, or Firm—John P. Wooldridge; Alan H. Thompson

(57) ABSTRACT

A system and method for doing both transmission mode and reflection mode three-dimensional ultrasonic imagining. The multimode imaging capability may be used to provide enhanced detectability of cancer tumors within human breast, however, similar imaging systems are applicable to a number of other medical problems as well as a variety of non-medical problems in non-destructive evaluation (NDE).

32 Claims, 8 Drawing Sheets

SYSTEM AND METHOD FOR ULTRASONIC TOMOGRAPHY

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to imaging, and more specifically, it relates to the use of ultrasound for tomographic imaging.

2. Description of Related Art

The ultrasound imaging has many advantages over ionizing radiation, especially, for example, in breast examinations. Employing acoustics to produce breast images, especially full three-dimensional reconstructions, while preserving the overall morphology and indicating various internal structures and regions such as ducts, epithelial tissue, masses, lesions, etc. is extremely powerful in detecting various carcinomas. Ultrasonic imaging has been used to image lumps in the body since there is a clear difference between a cyst and a suspected cancerous tumor. Recent research has demonstrated the potential for ultrasonic imaging to differentiate cancerous from non-cancerous lesions in the breast.

SUMMARY OF THE INVENTION

An aspect of the present invention includes a system and method comprising a first element designed to transmit first sound waves and receive first sound wave echoes; and a second element designed to receive second sound waves from said first element.

Another aspect of the present invention includes a system and method comprising recording ultrasonic tomographic transmission mode sound speed data and attenuation data to produce sound speed projection data and attenuation projection data; reconstructing said sound speed projection data and attenuation projection data using a straight ray approximation to produce a first reconstruction of a sound speed image and a first reconstruction of an attenuation image; and iteratively correcting said first reconstruction of said sound speed image and the first reconstruction of said attenuation image using a bent ray backprojection technique.

Another aspect of the present invention includes a method and system comprising recording reflection mode images of a target at a plurality of projection angles; calculating an error weighting factor; applying said error weighting factor to the reflection mode images; calculating impedance values at each angle to obtained weighted impedance images; and calculating density of the target from the plurality of projection angles.

DETAILED DESCRIPTION OF THE INVENTION

Figure 1:
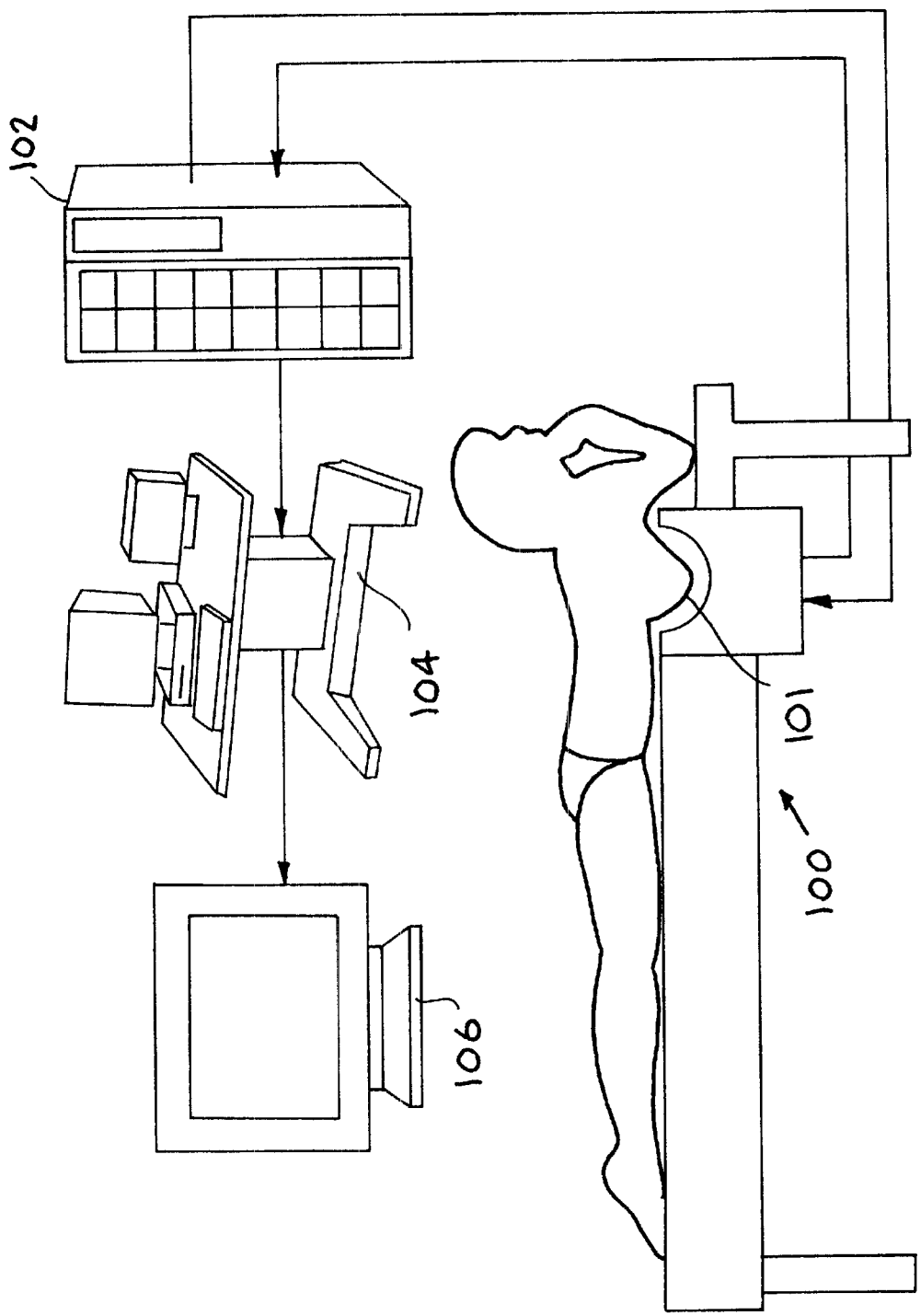
FIG. 1 is an illustration of an embodiment of the ultrasonic imaging system of the present invention.

A system and method of an embodiment of the present invention is shown in FIG. 1. FIG. 1 discloses a patient in a typical position for an examination. In the example shown, the patient's breast is the target 101 of the examination. (The terms object and target will be used interchangeably throughout this discussion). A breast examination is shown being performed for example purposes only and it is understood that many other types of examinations may be performed by the embodiments of the disclosed herein.

As shown in FIG. 1, a transducer assembly 100 acquires tomographic data from object 101 and is configured to achieve improved spatial resolution. The transducer assembly 100 is operatively coupled with drive, control and signal conditioning electronics 102. The drive, control and signal conditioning electronics 102 communicate with a high-speed computer 104 having a three-dimensional display 106. High-speed computer 104 is configured to control the tomographic data acquisition and renders the three dimensional images obtained from the data.

The transducer assembly 100 utilizes a plurality of transducer elements with the object 101 located in between. During typical operation, the transducer elements scan the object 101 to obtain projections (i.e., sections, slices) of the object until a full scan image is obtained. The transducer elements may either be designed to move with respect to the object during the scanning operation or remain stationary with respect to the object and perform an electronic scan. Typically, in an electronic scan, one or a group of transducer elements are sequentially operated to transmit and a separate plurality of transducer elements are configured to receive the transmitted signal or signals. In a typical design, the transducer elements may be micro-piezoelectric transducers. However, the transducer elements may also include capacitive, electromagnetic, electromechanical, inductive, photoconductive, and photovoltaic elements. The transducer elements may include transmitting transducer elements to produce radiation (e.g., ultrasonic plane waves) to illuminate the object 101, receiving transducer elements to measure the radiation from the object and transmitting/receiving transducer elements which may both produce and measure radiation. The transducer elements may be arranged in at least four different configurations. In these four configurations, the transducer elements may or may not be mounted on imaging heads in the transducer assembly.

Figure 2A:
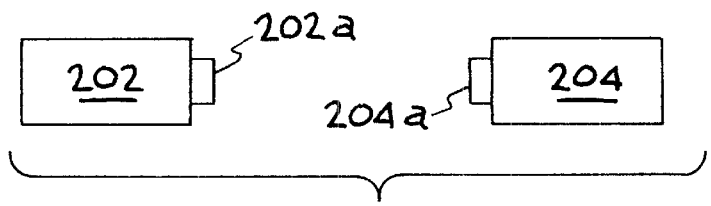
FIGS. 2A–2E illustrate different configurations of transducer elements that may be used in a transducer assembly in accordance with the present invention.
Figure 2B:
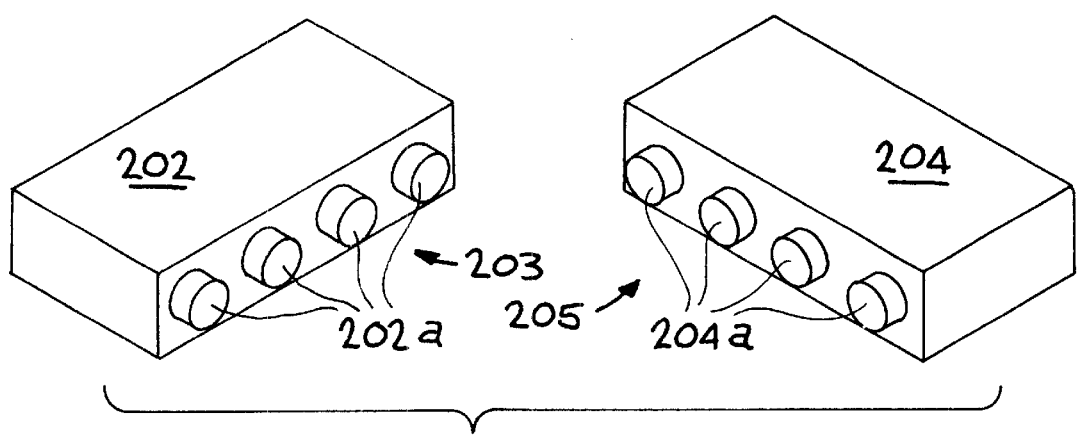

In a first configuration shown in FIG. 2A, a transmitting/receiving transducer element 202a is mounted on ultrasound imaging head (or first device) 202 and receiving transducer element 204a is oppositely mounted on ultrasound imaging head (or second device) 204. During data acquisition, the imaging heads 202 and 204 may be mechanically rotated around the target 101 and translated in a direction substantially orthogonal to the rotation direction to obtain volumetric or full-volume data measurements. The use of opposing ultrasound heads allows transmission mode data acquisition and increases the data acquisition rate in reflection mode. As will be discussed in more detail below, data acquisition may include both reflection mode imaging and transmission mode imaging. In transmission mode imaging one of the ultrasound imaging heads serves as the transmitter while the other imaging head positioned opposite acts as the receiver. A beam is passed through the target and the transmitted signal is measured on the opposite side. Reflection mode imaging comprises passing a beam into the target and measuring the reflection on the same side of the target. In reflection mode imaging either (or both) of the ultrasound heads may be configured to act as both the sender and the receiver. In the first configuration, during transmission mode imaging both transducer elements 202a and 204a are operated and in reflection mode imaging only transducer element 202a is used:

In a second configuration shown in FIG. 2B, the transducer elements 202a and 204a are arranged in one-dimensional arrays 203 and 205. A transducer array may have transducer elements patterned in a variety of arrangements. For example, arrays 203 and 205 may be made up of transducer elements which are each transmitting/receiving transducer elements (i.e., each transducer element adapted to both transmit and receive); arrays 203 and 205 may be arranged to have alternating transmitting and receiving transducer elements (i.e., interleaved transmitter and receiver transducer elements); or array 203 may have alternating transmitting and receiving transducer elements and array 205 may have just receiving transducer elements.

Figure 2E:
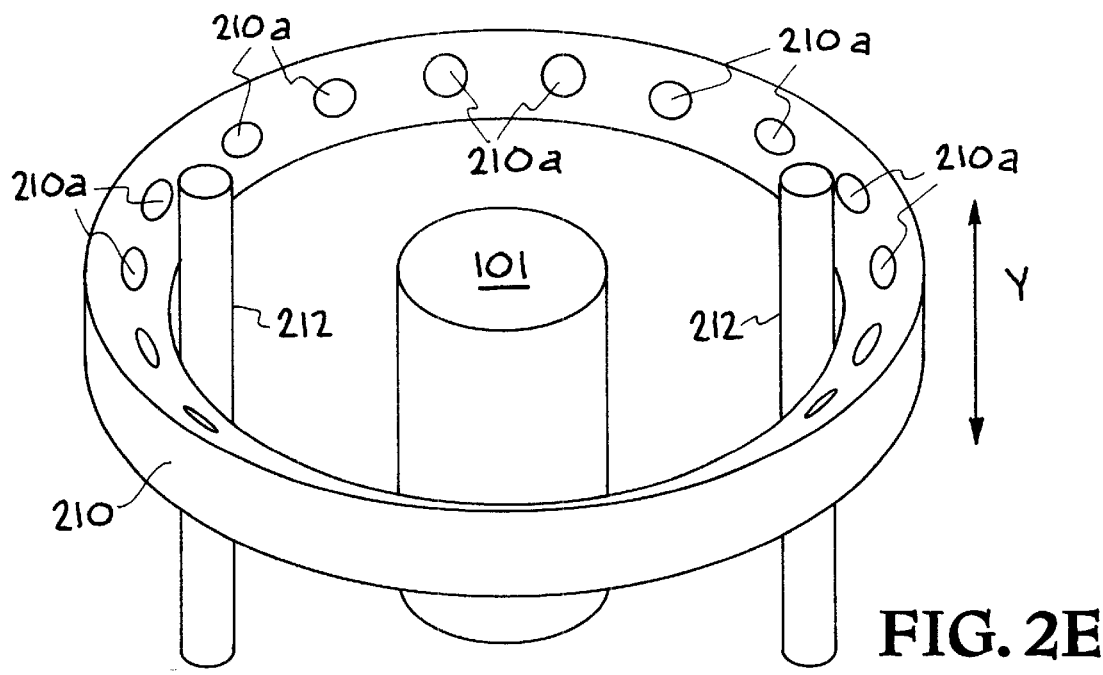
Figure 2C:
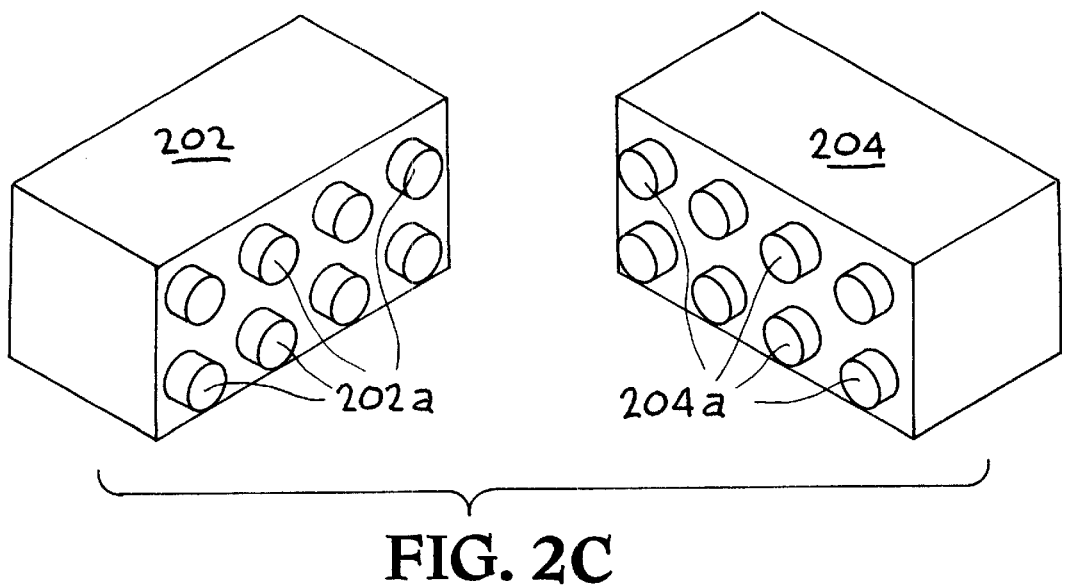

In a third configuration shown in FIG. 2C, the transducer elements 202a and 204a may be arranged in a two-dimensional array.

Figure 2D:
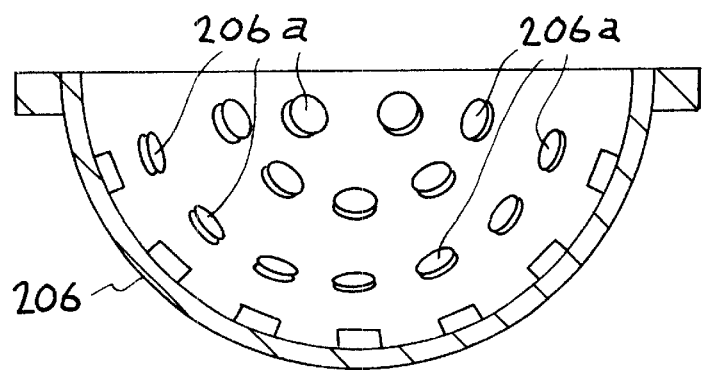

In a fourth configuration shown in FIG. 2D, a plurality of stationary transducer elements 206a are arranged in a dense array in a semi-circular pattern on a cylindrical surface 206 surrounding the target. As with the first three configurations, the transducer elements may each be transmitting/receiving transducer elements or interleaved transmitting and receiving transducer elements. As a result of this transducer element pattern surrounding the target 101, the transducer elements do not have to be designed to rotate around the target 101 and may remain stationary. Therefore, this fourth configuration results in greater speed efficiencies during data acquisition. During operation of this fourth configuration, individual transducer elements or sets of sub-arrays of transducer elements may be designed to electronically scan in a sequential manner around the object. When an individual transducer element or a sub-array of transducer elements are transmitting during data acquisition, the remaining transducer elements may be designated to receive these transmissions. These subarrays of transducer elements may then be sequentially addressed electronically by computer 104 and used to synthesize the same data acquisition scheme as with the mechanically rotated transmitter/receiver imaging head pair of the configuration shown in FIGS. 2A–2C. The subarrays of transducer elements may also be used to scan the object in more complex ways by means of synthetic aperture techniques.

In a fifth configuration shown in FIG. 2E, a plurality of transmitting/receiving transducer elements 210a are mounted on a ring 210 which encircles a target 101. Data acquisition is performed while the ring 210 and transducer elements 210a are in a stationary position. After each scan, the ring 210 may travel in a direction Y along the length of the target 101. In a typical application, the Y direction may be substantially the vertical direction. When a projection of the target 101 is being taken, the transducer elements 210a may transmit individually in sequence while substantially each of the other transducer elements 210a receive the transmitted signal until substantially all of the transducer elements 210a have transmitted. After a projection is obtained, the ring 210 may be moved in a series of predetermined increments along supports 212 until data acquisition is completed.

Figure 3A:
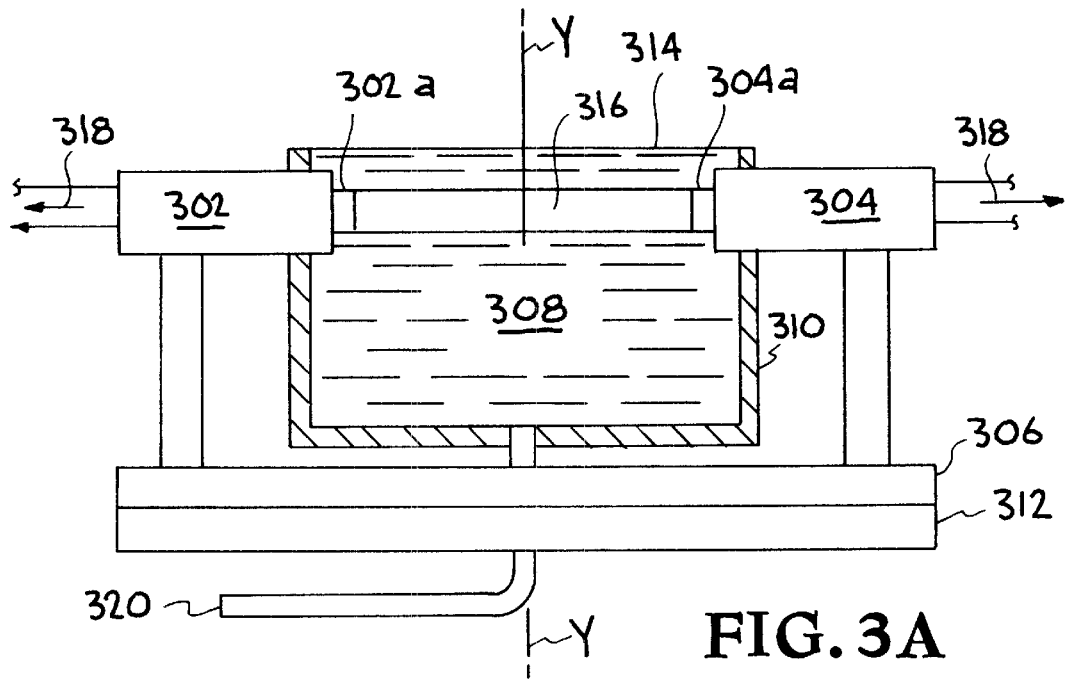
FIGS. 3A and 3B illustrate side and top views of an embodiment of the data acquisition system of the present invention.
Figure 3B:
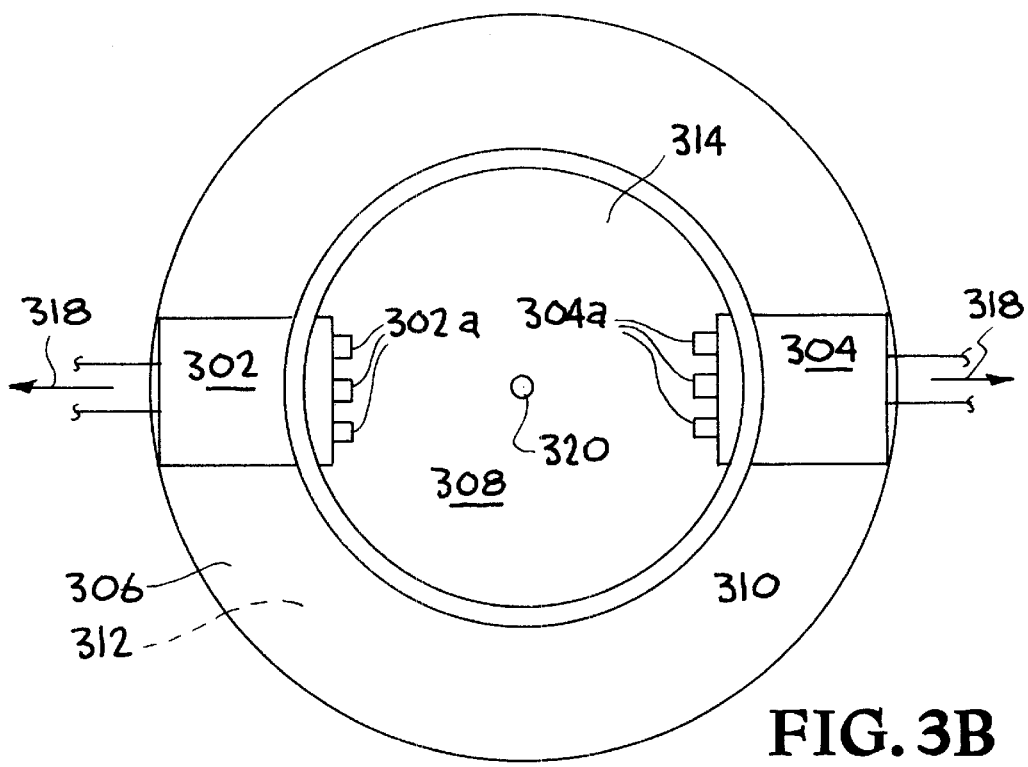

FIGS. 3A and 3B illustrate, for example purposes, the operation of the third configuration of transmitter and receiver ultrasound imaging heads. The imaging heads are labeled 302 and 304 in FIGS. 3A and 3B and each imaging head contains an array of transducer elements. In this embodiment the corresponding imaging heads 302 and 304 are mounted on the outer edge of the mechanical rotation stage 306 directly opposite to and facing each other by a predetermined distance to form a dual-head imaging system which may operate in both transmission and reflection modes. Transmission and reflection mode operation will be discussed in detail below. The object 101 (which is not shown in FIGS. 3A and 3B) from which projections are to be taken is located between the imaging heads 302 and 304 in cylindrical tank 310. The imaging heads 302 and 304 include transmitter and receiver arrays 302a, 304a and are mounted perpendicular to the axis of rotation Y—Y about the object. In this embodiment, imaging head 302 is a transmitting/receiving imaging head because transducer array 302a is capable of both transmitting and receiving operations and imaging head 304 is a receiving imaging head with transducer array 304a capable of just receiving operations. The transmitter and receiver arrays 302a, 304a obtain tomographic imaging data of a projection or slice 316 of the object.

In operation, the full image of the object may be obtained by translating the transmitter and receiver transducer imaging heads 302 and 304 around the rotation axis Y—Y by rotating the mechanical stage to obtain a slice 316 of the object 101. The remaining slices that make up the object are obtained by incrementally translating in the substantially orthogonal (e.g., vertical) direction the translation stage 312 to different positions or heights and then translating the transmitter and receiver transducer imaging heads 302 and 304 around the object. This process is repeated until full image data is obtained. The imaging heads' positions are adjusted after each set of two-dimensional projections is recorded. The full image will be compiled in computer 104 as a "stack of slices" from the two-dimensional projections which is also known as 2.5-Dimensional (2.5-D) imaging. The mechanical rotation stage 306 and the orthogonal translation stage 312 combine to form an accurate positioning mechanism for the imaging heads 302 and 304. A full three-dimensional image may then be reconstructed from a set of these two-dimensional projections. Arrows 318 indicate connections to the drive, control and signal conditioning electronics 102. Reference numeral 320 indicates an inlet from a leveling pump (not shown). The object is immersed in an acoustic coupling fluid 308 which is contained in the cylindrical tank 310 with an open top 314. Fluid 308 may have an acoustic impedance that closely matches that of the target so as to minimize reflection losses. The tank (or target chamber) 310 is placed at the center of the rotation stage 306 and the two ultrasound imaging heads 302 and 304 are mounted and sealed into openings on either side of the tank 310, or entirely immersed in the coupling fluid 308 within the tank 310, so that the active areas of the imaging heads 302 and 304 are in direct contact with the coupling fluid 308.

Transmission Mode Imaging and Analysis

Ultrasound transmission mode computed tomography (CT) is performed by first transmitting radiation (e.g., ultrasonic waves) through the target and recording the absorbed/scattered wave field with a receiver on the opposite side of the target. The data set produced by one such recording is known as a projection. The transmitter and receiver imaging head pair is then rotated about the target or otherwise moved to a new angular position with respect to the target, and a new projection is recorded. This is repeated to cover a number of angular positions over a large angular range. In general, the more closely spaced in angle the projections and the larger the angular range covered, the better the reconstructed image. Usually in transmission mode imaging, it is only necessary to acquire projections over a range of 180° for full coverage, however, in some special cases it is useful to take projections over 360°. The transducer assembly 100 will collect the set of data projections which may then be reconstructed in the high-speed computer 104 to produce a three-dimensional image.

Transmission mode imaging enables the measurement of an acoustic pressure wave not only to determine the attenuation (or absorption) of the wave, but also the time delay of the wave induced by the object or medium. The time delay information may then be used to calculate the speed of the wave which is inversely proportional to the time delay. Therefore, two criteria which are important to the reconstruction of the tomographic image—attenuation and speed—may be obtained. Compared to commonly used simple pulse-echo imaging scanners which can only "see" tissue interfaces and are therefore limited by scattering, ultrasonic transmission mode CT is more advantageous.

In transmission mode, sound speed and attenuation are determined by recording two separate parameters of the transmitted wave at each element of the receiver array for each projection. This may in principle be done with either continuous wave (CW) or pulsed operation; however, the CW approach is likely to have problems with multiple reflections that can be avoided with pulsed operation. With pulsed operation, sound speeds and attenuation coefficients within the object are reconstructed from measurements of arrival time and total amplitude change respectively. Reconstruction of each slice image from each component of the transmission mode projections may be accomplished by either direct Fourier inversion, or typically, by means of a filtered backprojection style algorithm (FBP). FBP is often a more efficient method of numerical reconstruction depending on the computer hardware used. However, more specialized versions of these reconstruction methods are described below.

Figure 4:
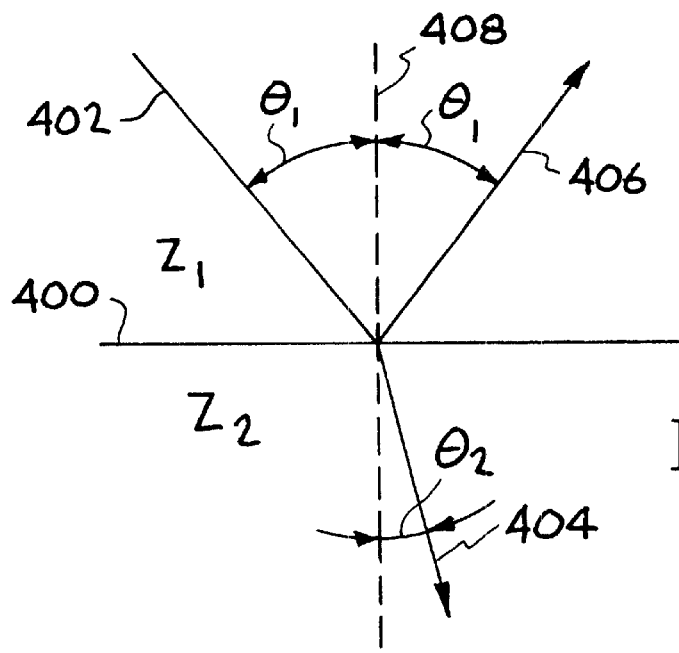
FIG. 4 illustrates reflection and refraction of incident acoustic radiation at an interface of differing acoustic impedances.

Initially, the tomographic reconstructions of the transmission mode data will be done under straight ray approximation—that is, assuming that the transmitted radiation propagates straight through the medium and is undeviated from its incident direction. In reality, when an ultrasonic beam propagates through tissue, it undergoes a deflection at every interface between tissues of different refractive indices. Using the straight ray assumption, first estimates of the sound speed and attenuation coefficient as a function of position in the object will be obtained. These estimates will then be iteratively corrected using a "bent ray" approach. This bent ray method uses the sound speed images generated at each iteration to calculate ray paths, accounting for refraction that occurs when the illuminating radiation passes through regions of varying acoustic impedance which have differing sound speed (real part of the refractive index). The ray paths, shown intersecting a medium barrier 40 in the object in FIG. 4, are calculated using Snell's law given by $$\frac{\sin\theta_1}{c_1} = \frac{\sin\theta_2}{c_2}$$

where $\theta 1$ is the angle of incidence of the illumination radiation 402, $\theta 2$ is angle of refraction of the refracted radiation 404, and C1 and C2 are the speed of sound in the two media respectively (reference numeral 406 indicates the reflected radiation). The acoustic impedances for the two different regions, $z_1$ and $z_2$, are given by $z_1 = \rho_1 c_1$ and $z_2 = \rho_2 c_2$, where $\rho$ represents the material density in a particular region. The bent ray backprojection technique starts with the sound speed image of the object and calculates the gradient of the sound speed image to obtain a vector field representing the normal to variations in the sound speed at every point within the object. It may also be necessary to pre-filter the sound speed image prior to calculating the gradient in order to remove unphysical single pixel variations (due to noise) which would in turn result in an inaccurate normal vector field. The normal at each point within the object (delineated as dotted line 408 in FIG. 4) is used in the calculation by Snell's law to find the refraction angle for each ray passing through the object at every point.

Based on these ray paths, the reconstructed images will be improved on each iteration, and a set of calculated projections will be obtained from the current "estimates" of both the sound speed and attenuation images. The iterations will continue until the calculated projections "match" the real recorded projection data as determined by an appropriate metric.

Figure 5A:
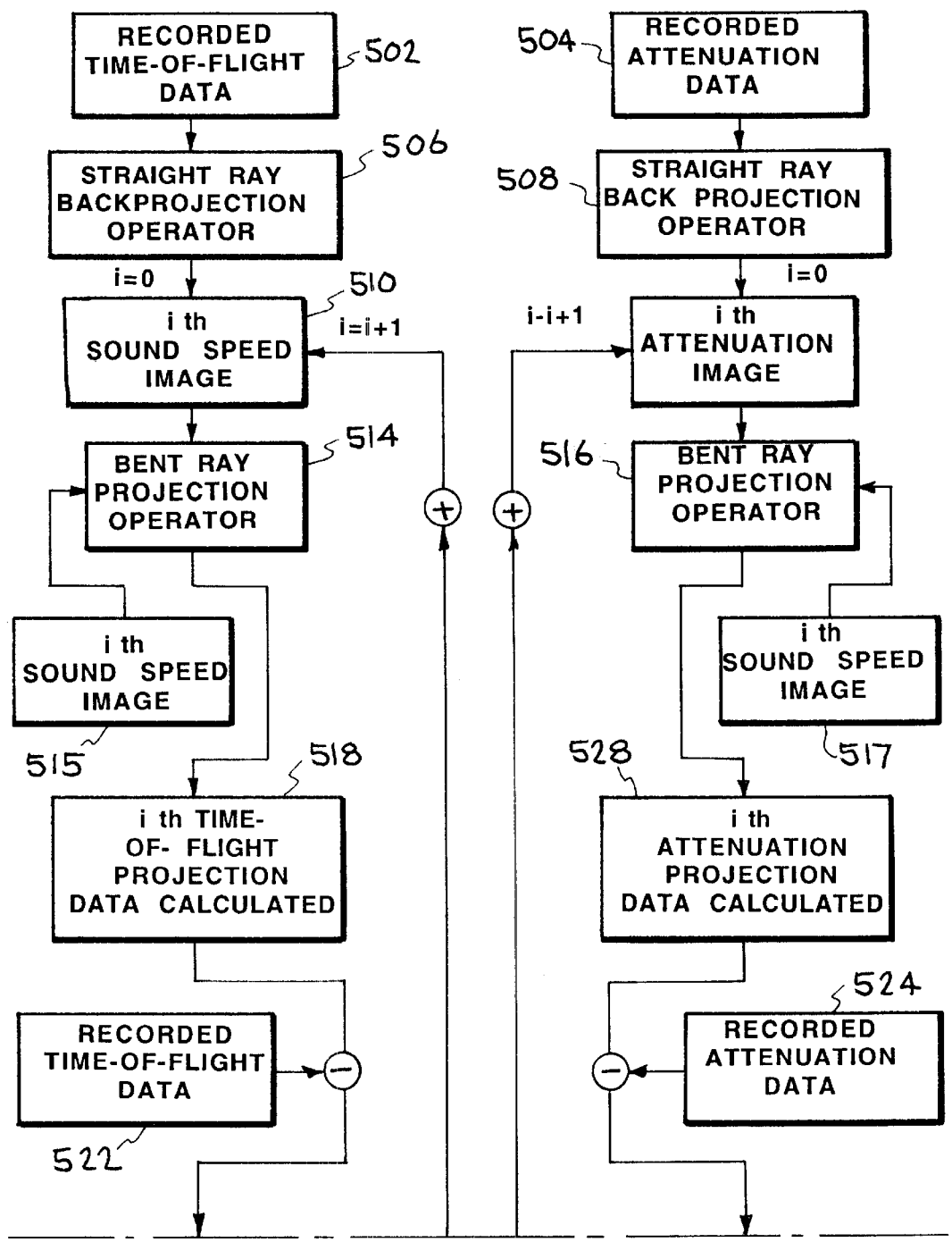
FIG. 5 illustrates a flow diagram of the Transmission Mode Process.
Figure 5B:
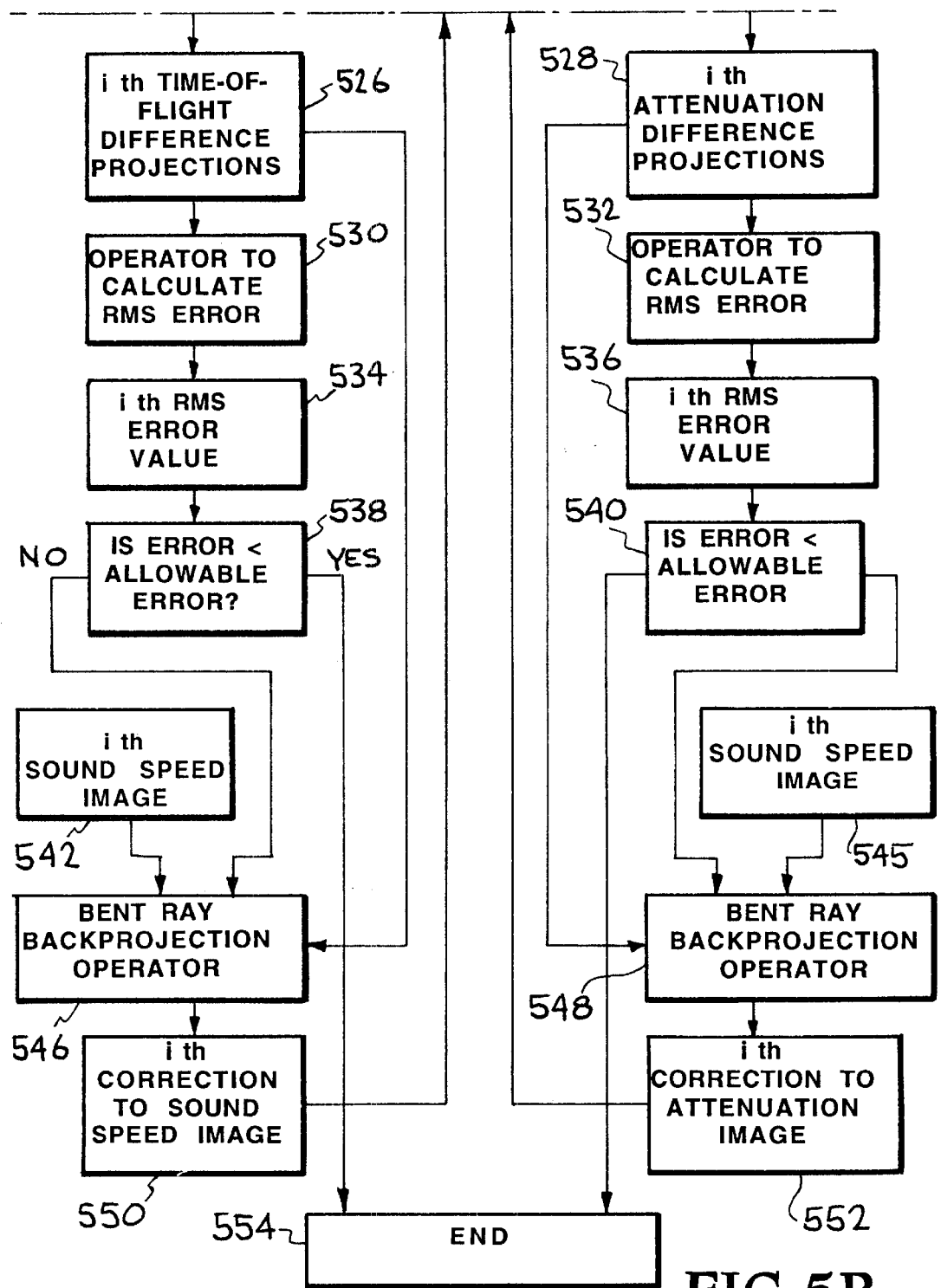

A flow diagram of the iterative Transmission Mode Process is shown in FIG. 5. The received transmission mode data consists of two separable parts: a time delay part 502, $\tau(\vec{s};\theta)$, which relates to sound speeds in the object and an amplitude part 504, $\alpha(\vec{s};\theta)$, which corresponds to attenuation coefficients within the object. The transmission mode data may first be separated into these two parts, and using a straight ray backprojection operator, 506 and 508, an initial estimate of the sound speed variations 510 within one slice of the object, $E_i^s(\vec{x})$, may be reconstructed from $\tau(\vec{s};\theta)$, and a separate estimate of the attenuation coefficient 512 at each point within the same slice of the object, $E_i^\alpha(\vec{x})$, may be produced from $\alpha(\vec{s};\theta)$. The calculated sound speed and attenuation projections $\rho_i^s(\vec{s};\theta)$ and $\rho_i^\alpha(\vec{s};\theta)$ 518 and 520, respectively, at the $i^{th}$ iteration are obtained from estimates $E_i^s(\vec{x})$ and $E_i^\alpha(\vec{x})$ through the bent ray projection operator $P_b(E_i^s(\vec{x}))$ 514, 516 which projects along bent rays depending on the current estimate of the sound speeds within the object, $E_i^s(\vec{x})$. The sound speed and attenuation projections 518 and 520 are calculated in the following manner:

$$p_i^s(\vec{s};\theta) = [P_b(E_i^s(\vec{x}))]E_i^s(\vec{x})$$
$$p_i^\alpha(\vec{s};\theta) = [P_b(E_i^s(\vec{x}))]E_i^\alpha(\vec{x})$$

$B_s$ and $B_b(E_0^s(\vec{x}))$ represent backprojection (image reconstruction) operators with straight rays and bent rays. Note that $B_b$ is a function of $E_i^s(\vec{x})$. Inputs 515 and 517 are used in the calculation of the backprojection bent ray operators. The generalized steps of the Transmission Mode Process are as follows. In a first step, the initial image or first estimate 510 and 512, will be obtained by $$E_0^s(\vec{x}) = [B_s]\tau(\vec{s}; \theta)$$

$$E_0^a(\vec{x}) = [B_s]\alpha(\vec{s}; \theta)$$

In a second step, on the first iteration, obtain the sound speed and attenuation projections 518 and 520:

$$p_1^s(\vec{s}; \theta) = [P_b(E_0^s(\vec{x}))]E_0^s(\vec{x})$$

$$p_1^a(\vec{s}; \theta) = [P_b(E_0^s(\vec{x}))]E_0^a(\vec{x})$$

In a third step, define the differences between the real projection data, 522 and 524, and the calculated projections, 518 and 520, after the first iteration $$\Delta_1 p^s(\vec{s}; \theta) = \tau(\vec{s}; \theta) - p_1^s(\vec{s}; \theta)$$

$$\Delta_1 p^a(\vec{s}; \theta) = \alpha(\vec{s}; \theta) - p_1^a(\vec{s}; \theta)$$

In fourth step, define an error value, $\eta_i$, 530 and 532, after each iteration as $$\eta_1 = \left\{ \frac{1}{MN} \sum_{\vec{s}}^{M} \sum_{\theta}^{N} \left[ (\Delta_1 p^s(\vec{s}; \theta))^2 + (\Delta_1 p^a(\vec{s}; \theta))^2 \right] \right\}^{\frac{1}{2}}$$

This error value is checked at this point on every iteration 534 and 536. The iterations are stopped when the error value is less than a constant, κ. If $\eta_i$<κ, 538 and 540 then proceed directly to the eighth step 554 where κ is a predetermined value based on experience with reconstructions of test objects and phantoms that will be used to characterize the imaging system performance.

If the error value is greater than κ, then after a fifth step using an algebraic reconstruction technique approach for example, calculate the correction to the current estimate in the following manner:

$$\Delta_1 E^s(\vec{x}) = [B_b(E_0^s(\vec{x}))]\Delta_1 p^s(\vec{s}; \theta)$$

$$\Delta_1 E^a(\vec{x}) = [B_b(E_0^s(\vec{x}))]\Delta_1 p^a(\vec{s}; \theta)$$

That is, backproject the differences using the bent ray backprojector and sound speed image input 542, 544 to find corrections to the current estimates 546 and 548. In a sixth step, the corrected estimates 550 and 552 are given by $$E_1^s(\vec{x}) = E_0^s(\vec{x}) + \Delta_1 E^s(\vec{x})$$

$$E_1^a(\vec{x}) = E_0^a(\vec{x}) + \Delta_1 E^a(\vec{x})$$

In a seventh step, increment the index i and go back to the second step which will then be:

$$p_2^s(\vec{s}; \theta) = [P_b(E_1^s(\vec{x}))]E_1^s(\vec{x})$$

$$p_2^a(\vec{s}; \theta) = [P_b(E_1^s(\vec{x}))]E_1^a(\vec{x})$$

In the eighth step, the end of the reconstruction process after J iterations. As discussed above, the looping (iterations) is stopped when the error value $\eta_j$<κ. The final sound speed image and attenuation coefficient image are $E_J^s(\vec{x})$ and $E_J^a(\vec{x})$ (510 and 512) respectively.

At this point, the number of iterations used may be printed and a plot of the error value with iteration number is generated and the program execution is stopped. Constraints may be applied to the reconstructed images on each iteration to improve the quality of the images, reject physically meaningless results and increase the rate of convergence (i.e., reduce the number of iterations needed). One important example of such a constraint is "positivity." Positivity refers to rejecting negative values for points in an image for which it is known that all values must be ≧0. In this case, all values of the attenuation coefficient image $E_i^a(\vec{x})$ must be ≧0 which represents the fact that no amplification of the transmitted radiation will occur anywhere within the object. A similar constraint can be applied to the sound speed image, $E_i^s(\vec{x})$, but in the form of requiring $E_i^a(\vec{x}) \geq E_{min}^s(\vec{x}) \forall \vec{x}$, where $E_{min}^s(\vec{x})$ is a predetermined minimum sound speed based on measured data taken on real human tissue.

Reflection Mode Imaging and Analysis

As previously discussed, reflection mode imaging may be performed using only one transducer array of the transducer assembly (for example, transmitting/receiving imaging head 302 in FIGS. 3A–3B). The transducer array is designed to conduct a B-scan. In B-scan operation, the transducer array elements first each transmit a short ultrasonic pulse with the relative timing between pulses sent from each transducer element set such that a focused beam is produced. The transducer array is then switched so that the transducer receiver elements are active and the reflected wave field is recorded at each transducer receiver element. The returned pulses at each element are then "phased" (i.e., their relative return times are adjusted) so as to produce a signal proportional to the reflection from the focal point of the transducer transmitter array. In practice, the depth-of-focus of the transducer array is usually set to be very long, and the return signals may be thought of as coming from a narrow line of points, or a beam, within the object perpendicular to the transducer array. The focal point, or beam, is then scanned through the object electronically under computer control by changing the phasing of the array elements and/or movement of the position of the sub-array. The time structure of the return signals provides the reflectivity in the dimension along the direction of the beam, and the scanning of the beam maps reflectivities in the other dimension(s).

Due to both attenuation in the object as well as limitations on the size and number of array elements, the image quality generally degrades as a function of depth (distance from the array). In addition, the measured reflectivity at a particular point within the object depends upon the angle of the reflecting surface with respect to the impinging ultrasonic beam. Reflection mode CT imaging can resolve these problems and improve both the quality (resolution and contrast) as well as the quantitative accuracy and content (reflectivity value and direction of reflecting surface normal) of the image. Due to losses in the object and the desire to map the normals to reflecting surfaces within the object, it is advantageous to acquire projections over a range of 360° for full coverage. As discussed above with reference to FIGS. 3A–3B, a full three-dimensional image can be built up in this manner if the transducer array is substantially perpendicular to the axis of rotation about the object to allow tomographic imaging of a "slice" of the object. The full image of the object can be obtained by translating the array along the direction of the rotation axis after each set of projections is recorded. The full image will be compiled as a "stack of slices" (i.e, 2.5-D imaging). This is performed by first acquiring a B-scan image of the object from one particular direction. The transducer array is then rotated about the object or otherwise translated to a new angular position with respect to the object, and a new projection is recorded. This is repeated to cover a number of angular positions over a large angular range. In general, the more closely spaced in angle the projections and the larger the angular range covered, the better the reconstructed image.

Reflection mode imaging provides a key parameter of the medium since the reflectivity, R, at an interface in the medium depends on the change in the acoustic impedance across the interface. The acoustic impedance is equal to the density times the sound speed. This information is valuable for diagnosis in itself, however, if the sound speed image from transmission mode data is known, one may obtain an image of the density variations within the object by using the reflection mode image information. This requires the acquisition of absolute values of impedances within the object from the reflection mode data. Since the reflectivity is proportional to the change in impedance at an interface, absolute impedance values may only be determined by launching the insonifying wave in a medium of known impedance, and using this information to reconstruct the absolute impedances from the sum of the changes in impedance along a path. Therefore, by using both the reflection mode image and the transmission mode image, the propagation speed, loss and density can be determined at all pixels within a slice of the object (or all voxels within the object for the full 3-D case) providing the maximum physical information available for diagnostic purposes.

As the ultrasound imaging heads rotate, or sets of sub-arrays electronically scan around the object, the reflection mode data will be taken from a large number of angles. Each B-scan will be a complete 2-D slice image (or a full 3-D volumetric image in the case of a 2-D ultrasonic array) of the object, not a simple projection as with transmission mode CT. The values of each pixel in the B-scan images depend on the reflectivity, R(x), within the object which in turn depends on the change in the impedance, $\Delta z(x)$. In addition to the theoretical reflectivity for normal incidence at an interface, there is a complex dependence on the angle of incidence of the insonifying radiation. Reflection 408 and transmission 402 at an interface 400 are depicted in FIG. 4 and the complete expression is given by:

$$R = \left[\frac{z_2\cos\theta_1 - z_1\cos\theta_2}{z_2\cos\theta_1 + z_1\cos\theta_2}\right]$$

where $z_1 = \rho_1 c_1$ and $z_2 = \rho_2 c_2$ (with the subscripts referring to density and sound speeds on either side of a boundary), and the incident and transmitted angles are given by Snell's law as previously discussed with respect to the Transmission Process Mode.

Figure 6:
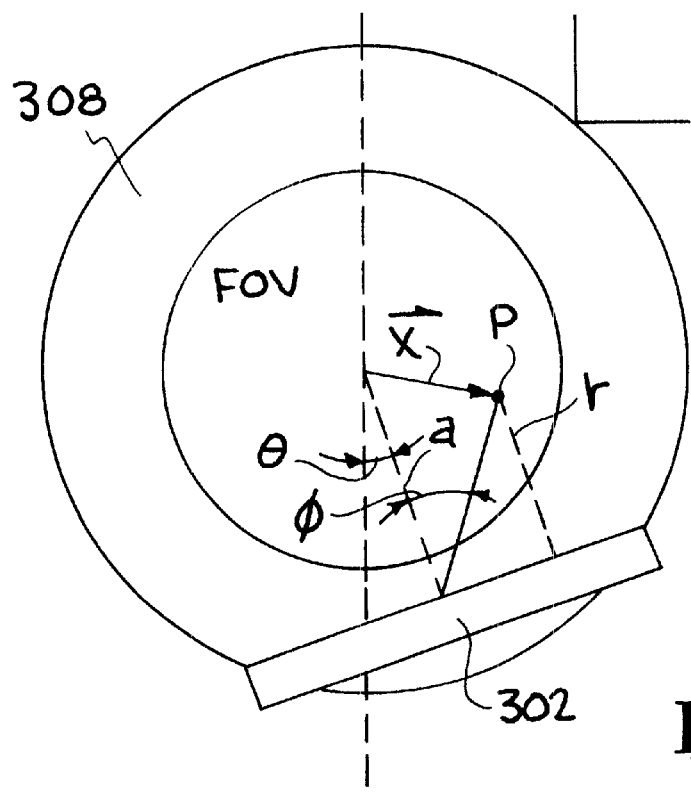
FIG. 6 illustrates reflection-mode imaging geometry.

B-scan imaging is performed using phased array technology to focus radiation on a point within the object, then selectively receive the reflected portion from that point. The beam is then swept in both angle and range to sample all the points within the field-of-view FOV as shown in FIG. 6. FIG. 6 illustrates a top view of the data acquisition system. Because of this, during measurement of R(x) at a point P within the object, portions of the insonifying radiation may reflect from several different interfaces between the point being imaged and neighboring points. The focal spot of the beam may also be shifted or distorted due to scattering from sound speed variations within the object. An additional complication is the angular dependence due to the cone angle of the impinging wavefront used in B-scan mode. This additional complication is greater at large range because the transmitted radiation must pass through a number of variations in the object. Another geometrical factor affecting the angular dependence due to the array geometry should also be included. R(x) is also dependent on the range (distance from the ultrasound head), r, because of attenuation losses that affect the insonifying radiation.

The reflection mode data will be used to determine the density, $\rho(x)$, within the object. In principle, it is possible to obtain values of the impedance, z(x), from the reflection mode images, but this requires converting information about $\Delta z(x)$ into absolute values of z(x). If z(x) is known, then the density function is:

$$\rho(x) = z(x)/c(x)$$

where c(x) is the sound speed within the object as before. The conversion of reflectivity, R(x) to impedance z(x) is difficult, however, because of the complicated dependencies of R(x) on both angle and range. One way to solve for z(x) would be to adopt a very computationally intensive iterative approach as was needed for the transmission mode reconstruction. This would start with c(x) reconstructed from the transmission mode data. An initial estimate of (x) would be made, then the impedance $z(x) = \rho(x)c(x)$ would be calculated. The B-scan data would then be modeled and compared with the real data. The estimate of $\rho(x)$ would then be updated iteratively based on the differences between the real and modeled data sets. However, such an approach would be unnecessarily complicated and time consuming for use with the reflection mode data, and therefore a more direct, non-iterative method may be used in the disclosed embodiment. The non-iterative method makes use of knowledge gained during the transmission mode and the abundance of data that will be collected in reflection mode.

Figure 7:
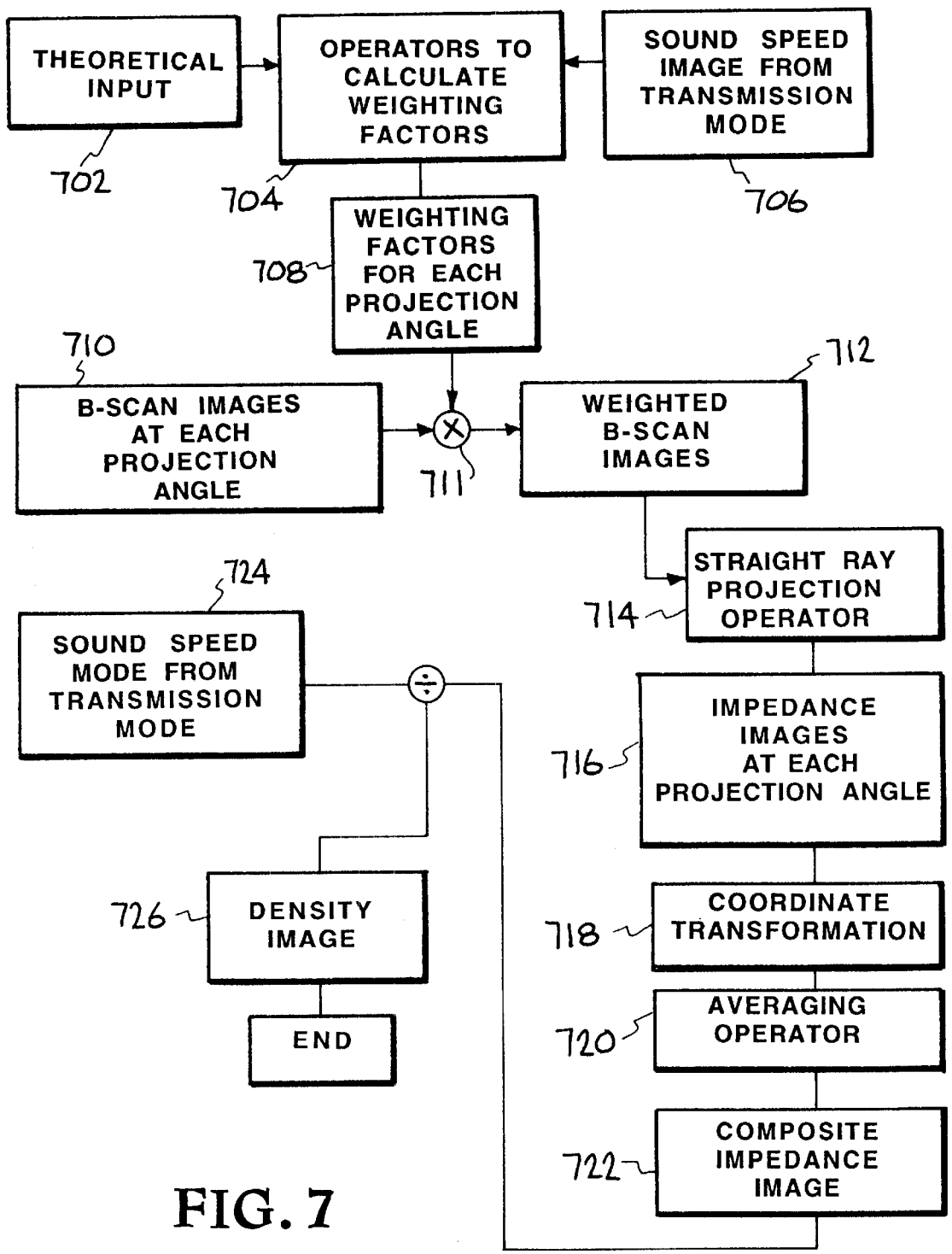
FIG. 7 illustrates a flow diagram of the Reflection Mode Process.

The Reflection-Mode Process is shown in FIG. 7 along with an accompanying description of the operations. The basic concept for this non-iterative approach is to reconstruct an estimate of z(x) within each slice of the object as a weighted average of the B-scans of that slice over all the projection angles. The weighting factor applied to each B-scan image will, in general, be a function of the projection angle, $\theta$, the beam angle, $\psi$, and the range, r (distance from the transducer array of the point being imaged) as illustrated by the imaging geometry of FIG. 6. Both $\psi$ and r are functions of the position of the point P, and depend on the type of ultrasound head used (i.e., linear or curved) and the details of how the B-scan is accomplished.

The weighting factor W ($\theta,\psi$, r) will account for losses in the object encountered by the insonifying wave, and the inaccuracies introduced in the measurement of R(x) due to the complicated dependencies on the angle of incidence of the insonification. In a sense, W ($\theta,\sigma$, r) represents a "confidence index" for each of the values of $\Delta z(x)$ at each projection angle. In its simplest form, the weighting factor would be a function of range only, W(r), accounting for estimated losses in the medium. The next level of complexity would be to include a theoretical dependence on the beam angle, $\psi$, while assuming no dependence on the projection angle, giving W($\psi$, r). Optimally, the weighting factor should incorporate the detailed information previously reconstructed from the transmission mode data to account for sound speed variations and losses at each point within the object yielding W($\theta,\psi$, r). Whichever weighing factor is used, W may be calculated prior to acquisition of the B-scan data and stored in a look up table. This will make calculation of the weighted averages quick and efficient regardless of the complexity of W. The exact choice of W will be based on numerical tests with highly characterized test objects and phantoms.

Once the weighting factor is applied to the set of B-scans, R(x, θ), absolute impedances will be calculated by starting in the coupling fluid 308 which has a known impedance, $z_0$, following straight ray paths inward, and using the following equation:

$$R = \frac{\Delta Z}{2\bar{Z}}, \quad \Delta Z = \rho_1 c_1 - \rho_2 c_2, \quad \bar{Z} = \frac{1}{2}(\rho_1 c_1 + \rho_2 c_2),$$

to successively calculate impedance values along each ray. This will produce a set of weighted images, z'(x,θ). These weighted images will then be summed over all projection angles to produce an estimate of the acoustic impedances, $E^z(x)$, everywhere within the slice. Once $E^z(x)$ is obtained, it is divided by the estimate of the sound speed, Ej(x), from the previous transmission mode reconstruction process to obtain an estimate of the density, $E^d$ (x). This method is illustrated in FIG. 7, where the theoretical input 702 and the transmission mode reconstructions 706 are combined with operators 704 to obtain the weighting factors for each projection angle 708. R(x,θ) 710 represents the set of B-scan images taken from all projection angles θ and W(θ,ψ, r) 708 represents the weighting factor which will be calculated based on the transmission mode reconstructions.

In a first step 708, the weighting factor is calculated as $$W(\theta, \varphi, r) = F_1[E_j^s(\vec{x}), \theta']F_2[E_j^c(\vec{x}), \theta']F_3[\varphi] \cdot F_4[r] \cdot \delta(\theta - \theta')$$

where $F_i[X]$ denotes a function of the argument X. The F[X] may be determined based on theoretical considerations and tests of the imaging system on highly characterized test objects and phantoms. In a second step 711, the weighted B-scans 712 are then calculated $$R'(\vec{x},\theta) = W(\theta,\psi,r) \cdot R(\vec{x},\theta)$$

In a third step 714, moving inward from the surface of the array along a series of parallel ray paths s, for each projection angle θ (as in the transmission mode) in quantized steps of size Δr:

$$z'_{r+\Delta r}(\vec{s}, \theta) = -z'_r(\vec{s}, \theta) \frac{R'(\vec{x}, \theta) - 1}{R'(\vec{x}, \theta) + 1}$$

By starting within the coupling fluid of known impedance $z_0$, there may be obtained from the above equation weighted images of the absolute impedance for each projection angle. In a fourth step 714, expressing z'(s, θ) as z'(s, r, θ) (see FIG. 2), convert $$z'(\vec{s},\theta) \rightarrow z'(\vec{x},\theta)$$

by using $$\vec{x} = x\hat{i} + y\hat{j}$$

where, for the 2-D case, $$x = s \cos \theta + (\alpha - r \sin \theta)$$

and $$y = s \sin \theta - (\alpha - r \cos \theta)$$

In a fifth step 716, the estimate of the absolute impedance values is obtained from the weighted impedance images at each projection angle by $$E^z(\vec{x}) = \frac{1}{N}\sum_i^N z'(\vec{x}, \theta_i)$$

were N is the total number of projection angles. In a final sixth step 726, the estimate of the density as a function of position within the object is computed $$E^d(\vec{x}) = \frac{E^z(\vec{x})}{E_j^s(\vec{x})}$$

and a density image is obtained which completes the Reflection-Mode process. A basic problem of ultrasound imaging is to determine the density and speed distributions by measuring the properties of waves launched through the target. The significance of using travel time and amplitude ratio as inputs to an image reconstruction method is that it provides two independent quantities, sound speed and attenuation, that may be used to identify tissues and lesions within the target. By using both transmission and reflectivity tomography modes speed, attenuation and reflectivity may be obtained, thereby increasing the capability of ultrasound to identify and characterize lesion within the target.

The disclosed embodiments incorporate high resolution three-dimensional ultrasonic imaging with sophisticated image reconstruction and post-processing for diagnosis into a practical, cost-effective system. The disclosed embodiments feature innovative hardware in the form of a dense sensor array capable of providing high resolution on the order of approximately 0.3 millimeters. Further the disclosed embodiments, use inversion methods that correct for curved rays and restore lost resolution and contrast in both transmission and reflection tomography modes. The disclosed embodiments may be nonmagnetic.

Therefore, the disclosed embodiments are non-ionizing, fast turnaround imaging methods and systems that may be made available at most clinics at a reasonable cost while providing a patient minimal discomfort.

The disclosed embodiments further show a system and method for doing both transmission mode and reflection mode three-dimensional ultrasonic imagining for mammography. The system could also be used in doppler (reflection) mode to map blood flow velocity in three-dimensions. The multimode imaging capability may be used to provide enhanced detectability of tumors (e.g., cancer) within a human breast, however, similar imaging systems are applicable to a number of other medical problems as well as a variety of non-medical problems in non-destructive evaluation (NDE). Therefore, the system disclosed may be used to examine tissue (e.g., breast), body parts, appendages, and internal body parts (e.g., organs).

This ultrasonic hardware system disclosed in the embodiment provides the means to manipulate ultrasound generators and receivers to allow data acquisition for target imaging. This system supports various modes of scanning components for tomographic, holographic and standard ultrasonic image reconstructions.

The foregoing description has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A method comprising:
   recording ultrasonic tomographic transmission mode sound speed data and attenuation data to produce sound speed projection data and attenuation projection data;
   reconstructing said sound speed projection data and attenuation projection data under a straight ray approximation to produce a first reconstruction of a sound speed image and a first reconstruction of an attenuation image; and
   iteratively correcting said first reconstruction of said sound speed image and said first reconstruction of said attenuation image using a bent ray backprojection technique, wherein said bent ray backprojection technique calculates a gradient of said sound speed image to obtain a vector field representing the normal to variations in sound speed at every point within said medium under test.

2. The method of claim 1, wherein said first reconstruction of said sound speed image and said first reconstruction of said attenuation image are improved on each iteration to produce a set of calculated projections.

3. The method of claim 2, wherein said first reconstruction of said sound speed image and said first reconstruction of said attenuation image are iterated until said calculated projections match a predetermined metric for comparison to said sound speed projection data and attenuation projection data.

4. The method of claim 2, wherein said biological tissue comprises breast tissue.

5. The method of claim 1, wherein the step of reconstructing said sound speed and said attenuation projection data is carried out with a filtered backprojection algorithm.

6. The method of claim 1, wherein the step of reconstructing said sound speed and said attenuation projection data is carried out with a direct Fourier inversion.

7. The method of claim 1, wherein said bent ray backprojection technique uses said sound speed image to calculate ray paths.

8. The method of claim 7, wherein said ray paths are calculated with Snell's law.

9. The method of claim 1, further comprising:
   pre-filtering said sound speed image prior to calculating said gradient in order to remove unphysical single pixel variations which would in turn result in an inaccurate normal vector field.

10. The method of claim 1, wherein the step of iteratively correcting said first reconstruction of said sound speed image and said first reconstruction of said attenuation is carried out with an algebraic reconstruction technique.

11. The method of claim 1, further comprising:
    producing said ultrasonic tomographic transmission mode data by transmitting an ultrasonic wave through a medium under test to produce a transmitted wave and detecting said transmitted wave.

12. The method of claim 1, wherein said medium under test comprises biological tissue.

13. The method of claim 1, wherein said ultrasonic wave comprises a plane wave.

14. The method of claim 1, wherein said ultrasonic wave is transmitted by a transmitter comprising at least one transducer.

15. The method of claim 14, wherein said transmitted wave is detected with at least one receiver.

16. The method of claim 15, wherein said transmitter and receiver (T/R) pair is moved by rotating said T/R pair about said medium under test.

17. The method of claim 16, wherein said transmitter and said receiver array comprise at least one pair of one-dimensional devices mounted perpendicular to an axis of rotation about said medium under test to allow tomographic imaging of a slice of said medium.

18. The method of claim 1, wherein said ultrasonic wave is transmitted by a transmitter comprising an array of transducer elements.

19. The method of claim 18, wherein said transmitter and receiver comprises a transmitter/receiver (T/R) pair that is moved to a new angular position with respect to said medium under test and a new ultrasonic wave is transmitted through said medium under test.

20. The method of claim 14, wherein said transmitter and said receiver array comprise at least one pair of two-dimensional area devices set parallel to each other and separated by a predetermined distance so that said medium under test fits between them.

21. The method of claim 20, wherein the full image of said medium under test can be obtained by translating said pair along the direction of said axis of rotation after each said projection is detected, wherein a full image will be compiled as a stack of slices.

22. The method of claim 15, wherein said T/R pair is moved with a mechanical stage.

23. The method of claim 22, wherein sub-arrays of said dense array are sequentially addressed electronically and acquire data at a plurality of angular positions around said medium under test.

24. The method of claim 1, wherein said ultrasonic wave is transmitted and received by a dense array of transducer elements, each of said transducer elements acting as either a transmitter or a receiver.

25. A computer-useable medium embodying computer program code for transmission mode ultrasonic tomography by executing the steps of:
    recording ultrasonic tomographic transmission mode sound speed data and attenuation data to produce real recorded sound speed projection data and attenuation projection data;
    reconstructing said real recorded sound speed projection data and attenuation projection data under a straight ray approximation to produce a first reconstruction of a sound speed image and a first reconstruction of an attenuation image; and
    iteratively correcting said first reconstruction of said sound speed image and said first reconstruction of said attenuation image using a bent ray backprojection technique, wherein said bent ray backprojection technique calculates a gradient of said sound speed image to obtain a vector field representing the normal to variations in sound speed at every point within said medium under test.

26. The computer-useable medium of claim 25, wherein said first reconstruction of said sound speed image and said first reconstruction of said attenuation image are improved on each iteration, to produce a set of calculated projections, wherein said first reconstruction of said sound speed image and said first reconstruction of said attenuation image are iterated until said calculated projections match a predetermined metric for comparison to said real recorded sound speed projection data and attenuation projection data.

27. The computer-useable medium of claim 25, wherein the step of reconstructing said real recorded projection data is carried out with a filtered backprojection algorithm.

28. The computer-useable medium of claim 25, wherein the step of reconstructing said real recorded projection data is carried out with a direct Fourier inversion.

29. The computer-useable medium of claim 25, wherein said bent ray backprojection technique uses said sound speed images to calculate ray paths, accounting for refraction that occurs when the illuminating radiation passes through regions of varying acoustic impedance which have differing sound speed.

30. The computer-useable medium of claim 25, wherein said ray paths are calculated with Snell's law.

31. The computer-useable medium of claim 25, further comprising pre-filtering said sound speed image prior to calculating said gradient in order to remove unphysical single pixel variations.

32. The computer-useable medium of claim 25, wherein the step of iteratively correcting said first reconstruction of said sound speed image and said first reconstruction of said attenuation is carried out with an algebraic reconstruction technique.

* * * * *